United States Patent [19]

Garwood et al.

[11] Patent Number: 4,502,479

[45] Date of Patent: Mar. 5, 1985

[54] WATER-ACTIVATED CASTING MATERIAL

[75] Inventors: Donald C. Garwood; Shiraz A. Kathiriya, both of Costa Mesa, Calif.

[73] Assignee: Minnesota Mining and Manufacturing Company, St. Paul, Minn.

[21] Appl. No.: 72,203

[22] Filed: Sep. 4, 1979

[51] Int. Cl.³ ............................................. A61F 13/04
[52] U.S. Cl. .................................................... 128/90
[58] Field of Search .................. 128/90, 87 R, 87 A, 128/88, 89 R, 92, 91

[56] References Cited

U.S. PATENT DOCUMENTS

| | | | |
|---|---|---|---|
| 3,421,501 | 1/1969 | Beightol | 128/90 |
| 3,630,194 | 12/1971 | Boardman | 128/90 |
| 3,686,725 | 8/1972 | Nisbet et al. | 128/90 |
| 3,881,473 | 5/1975 | Corvi et al. | 128/90 |
| 4,052,282 | 10/1977 | Kubushiro | 128/90 |
| 4,105,025 | 8/1978 | Wang et al. | 128/90 |
| 4,131,114 | 12/1978 | Kirkpatrick et al. | 128/90 |
| 4,134,397 | 1/1979 | Gianakakos et al. | 128/90 |

FOREIGN PATENT DOCUMENTS 2357931 5/1975 Fed. Rep. of Germany .
2651089 5/1978 Fed. Rep. of Germany .

OTHER PUBLICATIONS

"3rd Annual Meeting of the Society for Biomaterials", Lysaght et al., 1977.

Primary Examiner—Benjamin R. Padgett
Assistant Examiner—T. J. Wallen
Attorney, Agent, or Firm—Donald M. Sell; James A. Smith; Carolyn A. Bates

[57] ABSTRACT

An orthopedic casting material is disclosed having improved strength and porosity characteristics. The casting material comprises a fabric which is made from a high modulus fiber and has a thickness between 0.020 and 0.045 inches and a mesh size of 20 to 200 openings per square inch. The fabric is impregnated with a reactive resin which hardens by wetting with a curing agent.

8 Claims, No Drawings

WATER-ACTIVATED CASTING MATERIAL

The present invention pertains to the application of orthopedic casts, and in the preferred embodiment, to the application of orthopedic casts formed of moisture-curing plastic material.

Orthopedic casts for use in the treatment of bone fractures or other conditions requiring immobilization of a body member are generally formed from a strip of fabric or scrim material impregnated with a substance which hardens into a rigid structure after the strip has been wrapped around the body member. The hardening substance traditionally used is plaster-of-paris. Plaster-of-paris casts, however, have a number of attendant disadvantages including a low strength-to-weight ratio resulting in a finished cast which is very heavy and bulky. Plaster-of-paris casts breakdown in water thus making bathing or showering difficult. Also, plaster-of-paris casts are not air-permeable and do not allow for evaporation of moisture from the skin beneath the cast. This may lead to skin irritation or infection. These disadvantages, as well as many others, have stimulated the search for other hardening substances having improved properties over plaster-of-paris.

Certain plastic and plastic-reinforced materials have gained wide attention as potential replacements for plaster-of-paris in orthopedic casts. Plastic casts are generally much lighter than plaster-of-paris, impervious to water and priovide excellent X-ray clarity. However, they have not gained broad acceptance among physicians and cast technicians due to their failure to meet certain performance requirements. A good plastic casting material must be safe to apply and non-irritating to the skin of the wearer. Thus, resins which give off toxic volatile materials or which expose the body to unsafe heat levels during application are unacceptable. A suitable resin must allow sufficient "working time" e.g., 8 to 10 minutes, in which the wrapping is accomplished and the cast is pressed into shape. After the cast is shaped, the resin should harden rapidly, e.g., in 15–30 minutes, into a rigid, high-strength, weight-bearing cast. In addition to the foregoing requirements, a good plastic casting material should provide good lamination between the fabric layers of the cast, be porous enough to allow evaporation of moisture from the skin, have good X-ray clarity, low flammability and a shelf life of at least nine months under room temperature storage conditions. A number of attempts have been made heretofore to provide a plastic casting material meeting the foregoing criteria.

A significant advance in the art is disclosed in U.S. Pat. Nos. 3,421,501 and 3,881,473. The casting materials disclosed in these patents comprise a flexible fabric impregnated with an ultraviolet light-curing polymer. The major disadvantage associated with this type of cast material is the need for an ultraviolet light source which is unavailable in many hospitals and doctors' offices.

U.S. Pat. No. 4,105,025 discloses a cast-forming bandage material comprising a substrate such as a perforated fabric or net-like structure impregnated or coated with a crystallized polyurethane polymer material. The bandage is heated to melt the polymer prior to application to the body member. The bandage is applied immediately or allowed to cool down to room temperature prior to application and formed into the desired shape. Upon standing at room temperature, the polyurethane polymer crystallizes into a rigid cast. Disadvantages of this type of casting material, as well as other casting materials containing thermoplastic resins, include the necessity to heat the material prior to application and the danger of applying hot materials to the skin.

As an alternative to thermoplastic materials which are polymerized prior to use and merely softened to render them flexible enough for application to the body member, other casting materials and orthopedic appliances are known wherein the resin is cured after application to the body member. Generally, this involves exposing the resin to a second chemical reactant or catalyst. An example of such a system is a fabric or scrim material impregnated with a polyurethane prepolymer which reacts with water as the second chemical reactant to initiate curing. The prepolymer-treated bandage is soaked in water prior to application to the body member. The wet bandage is then applied to the body member by wrapping in much the same way as a plaster-of-paris cast is applied. The bandage hardens into a rigid structure in a matter of minutes. A paper by Lysaght and Rich describing such a casting material was presented at the 3rd Annual Meeting of the Society for Biomaterials, 9th Annual International Biomaterial Symposium, New Orleans, La. (1977). These observers found that fine-woven fiberglass as the scrim material provides a cast with the highest strength-to-weight ratio and best overall feel. No specific information regarding the fiberglass fabric was disclosed.

Another casting material comprising a fabric impregnated with a water-curable polyurethane prepolymer is disclosed in German Offenlegungsschrift No. 26 51 089. The essence of the invention disclosed therein resides in the use of prepolymers prepared from aromatic polyisocyanates and tertiary amine N-containing polyols. A product currently marketed in the United States under the trademark Cutter Cast ® by a subsidiary of the company owning the aforementioned German Patent Application comprises a dacron/cotton (65/35) fabric and a water-cured polyisocyanate prepolymer.

From the foregoing discussion, it is apparent that the prior art has discovered improved plastic casting materials which solve many of the problems previously associated with such materials. The polyurethane casting materials discussed immediately above are relatively safe and easy to apply to the body member. They are water-cured and give off little exotherm. Additionally, the cast remains soft and moldable long enough to permit shaping into the desired configuration yet cure relatively fast to permit the patient to leave the hospital or doctor's office within a short time. These prior art casts do, however, suffer from lack of strength and porosity. This is particularly bothersome in the case of leg casts which must be weight-bearing in a relatively short time after application to permit the patient to walk around.

The present invention solves the aforementioned problem by providing a plastic casting material which has improved strength. The casting material of the invention provides improved strength and rigidity within 20–30 minutes after application with a minimum of overlapping layers. The solution to the problem lies primarily in the scrim or tape material which is impregnated with the resin.

According to the present invention there is provided an orthopedic casting material comprising a high strength and high modulus fabric made from a fiber having an initial modulus of elasticity greater than $8 \times 10^6$ pounds per square inch. The fabric has a thickness between 0.020 and 0.045 inch and a mesh size of 20 to 200 openings per square inch and is impregnated with a reactive resin which hardens by wetting with a second reactive chemical or catalyst solution (curing agent). After wetting with the curing agent (e.g., by soaking for about 30 seconds) the material, when wrapped upon itself to form a cylindrical laminate of eight or less layers will have a load-bearing strength sufficient for weightbearing (for a 2-inch diameter cylinder) 20 pounds per inch of cylinder length within 30 minutes after exposure to water.

The term "high modulus" as used herein to describe the fabric component of the casting material refers the degree of resistance to deformation or bending and is expressed in terms of the modulus of elasticity. Modulus of elasticity is the ratio of change in stress to the change in strain which occurs when a fiber is mechanically loaded. The initial modulus of elasticity of the fiber should be greater than about $8 \times 10^6$ lbs/square inch. Such fibers include continuous filament E-fiberglass, polyaramid filament known as Kevlar ® 49 (available from E. I. DuPont de Nemours and Company), ceramic fibers such as Nextel ® (available from 3M Company), continuous filament graphite such as Thornel ® (available from Union Carbide Corp.), boron fiber (such as made by Avco Corp.), and metal fibers such as stainless steel filaments which when fine enough can be formed into fabrics by weaving or knitting. These high modulus fibers impart a high degree of strength and rigidity to the cast. They may be combined with low to intermediate modulus materials when the flexibility of such yarns enables easier fabrication of the fabric. Low modulus fibers are those having an initial modulus of elasticity of less than about $3 \times 10^6$ lbs/in$^2$ and include cotton, polyester (such as "Dacron"), polypropylene, "Orlon", "Dynel" ® (Union Carbide), "Nomex" ® (Dupont) and nylon. An example of a fiber with an intermediate modulus is polyvinyl alcohol fiber known as "Kuralon" (available from Kuraray Co., Ltd.). Although hybrid fabrics are useful in making orthopedic casts, a majority of high modulus fiber is necessary for adequate cast rigidity and strength.

The preferred fabric for use on the casting material of the invention is made of fiberglass fibers, particularly Raschel knit fiberglass fibers. The Raschel knit fabric affords a lateral stretchability without lengthwise stretchability in the tape. Lateral stretch provides a high degree of conformability to the body member. The resistance to lengthwise stretch in the tape is desirable to prevent undesirable restriction of circulation within the body member.

The preferred fabric is a 3-bar Raschel knit of 18 gg knitted from a single fiberglass yarn construction called ECC 75 1/0 (available from Owens Corning). One yarn end is used per guide needle. Bar 1 executes a chain stitch while bar 2 overlaps four needles. Bar 3 lays in a yarn longitudinally within each wale. This fabric is porous enough to allow water penetration of the cast and air circulation through the cast.

In addition to structural strength provided by the high modulus fiber, the fabric must have certain textural characteristics. The textural characteristics of the fabric, especially its surface area, porosity and thickness, affect the thoroughness and rapidity with which the curing agent becomes mixed or dissolved in the resinous component impregnated into the fabric. In one extreme in which the curing agent e.g., water, contacts only the surface of the resin, the surface of the resin would become hardened, but the resin would remain fluid below the hardened surface and not contribute to the strength of the cast. Furthermore, the hardened surface often impedes the permeation of the curing agent into the bulk of the still fluid resin. In such a case the desired rapid hardening is not achieved, and the bulk of the resin may never become hard because the surface is impenetrable to the curing agent. It has been discovered that such behavior can be avoided if the resinous layer is kept thin. This can be achieved at useful loadings of resin into the fabric if the fabric is selected to be thin and to have a high surface-to-volume ratio.

In determining the optimum thickness of the fabric, the need to keep the resinous layer thin to promote complete curing must be balanced with the need to minimize the number of layers in the cast. Practical considerations related to the ease of wrapping an orthopedic cast limit the number of layers of tape that it is convenient to apply. For most efficient cast application it is desired that the cast be comprised of no more than 6 to 8 layers of overlapping wraps of tape and preferably 4 to 5 layers of tape. A sufficient amount of material must be applied in these few layers to achieve the desired ultimate cast strength and rigidity. The thinner the fabric, the more wraps of tape have to be made to achieve adequate strength and rigidity. It has been found that a fabric thickness between 0.020 and 0.045 inch and preferably between 0.022 and 0.035 inch, achieves the optimum balance between good resin curing and a minimum number of wraps.

The fabric should be a mesh, i.e., it should have openings through it to enable the curing agent to penetrate into the roll and expose all parts of the resin. Openings in the fabric also facilitate circulation of air through the finished cast and evaporation of moisture from beneath the cast. This contributes to the patient's comfort and the maintenance of healthy skin under the cast. In the case of casting materials whose strength or rigidity is not degraded by exposure to water, cast porosity also enables rapid drying after bathing or following various forms of hydrotherapy or fluid rinsing for tissue debridement. The fabric should have a mesh size 20 to 200 openings per square inch, and preferably 80 to 150 openings per square inch.

The fabric used in the casting material is generally formed in rolls of various widths, generally from one inch to six inches wide. The fabric is impregnated with the curable resin material in an amount, in terms of volume, of from one to three times the volume of the material forming the fabric, and in the preferred embodiment employing a fiberglass fabric of from 40% to 50% by weight of the impregnated casting material. The term "impregnate" is used to describe the condition in which the polymer is thoroughly intermingled with and in surrounding relation to the threads or fibers of the fabric and does not necessarily indicate that the resin is to any extent adsorbed by the fibers themselves. Generally, the resin solution will flow into the capillary spaces between contiguous filaments of the fabric and will become rigidly bonded to the fabric upon curing.

The amount of resinous component applied to the fabric must be sufficient for the formation of a strong interlayer laminate bond but not so much as to occlude the porosity and unnecessarily thicken the resin film which should be thin for rapid and complete hardening. Excessive resinous component may also cause the casting tape to be messy to handle because of stickiness or dripping and transfer of resin.

The resin used in the casting material of the invention may be any curable resin which will satisfy the functional requirements of an orthopedic cast. Obviously, the resin must be nontoxic in the sense that it does not give off significant amounts of toxic vapors during curing which may be harmful to either the patient or the person applying the cast and also that it does not cause skin irritation either by chemical irritation or the generation of excessive heat during curing. Furthermore, the resin must be sufficiently reactive with the curing agent to insure rapid hardening of the cast once it is applied but not so reactive that does not allow sufficient working time to apply and shape the cast. Initially, the casting material must be pliable and formable and should adhere to itself. Then in a short time following completion of cast application, it should become rigid and strong to support loads and stresses to which the cast is subjected by the activities of the wearer. Thus, the material must undergo a change of state from a fluid-like condition to a solid, hard condition in a matter of minutes.

The preferred resins are those cured with water. A number of classes of water-cured resins known in the art are suitable, including polyurethanes, cyanoacrylate esters, and, when combined with moisture sensitive catalysts, epoxy resins and prepolymers terminated at their ends with trialkoxy- or trihalo- silane groups. For example, U.S. Pat. No. 3,932,526 discloses that 1,1-bis(-perfluoromethylsulfonyl)-2-aryl ethylenes cause epoxy resins containing traces of moisture to become polymerized.

Resin systems other than those requiring water-curing may be used, although the use of water to activate the hardening of an orthopedic casting tape is most convenient, safe and familiar to orthopedic surgeons and medical casting personnel. The principles disclosed herein regarding the modulus of elasticity, porosity and thickness of the fabric are applicable to resin systems such as that disclosed in U.S. Pat. No. 3,908,644 in which a bandage is impregnated with difunctional acrylates or methacrylates, such as the bis-methacrylate ester derived from the condensation of glycidyl methacrylate and bisphenol A (4,4'-isopropylidenediphenol). The resin is hardened upon wetting with solutions of a tertiary amine and an organic peroxide. Also, the water may contain a catalyst. For example, U.S. Pat. No. 3,630,194 proposes an orthopedic tape impregnated with acrylamide monomers whose polymerization is initiated by dipping the bandage in an aqueous solution of oxidizing and reducing agents (known in the art as a redox initiator system). The strength, rigidity and rate of hardening of such a bandage is subject to the factors disclosed herein.

The preferred resins for use in the present invention are polyurethanes. Suitable polyurethane systems are disclosed, for example in U.S. Pat. No. 3,373,741 and in German Offenlegungsschrift No. 2651089. The following disclosure relates primarily to the preferred embodiment of the invention wherein water-curable polyurethane resins are employed.

It is preferred to coat the resin onto the fabric as a polyisocyanate prepolymer formed by the reaction of an isocyanate and a polyol. It is preferred to use an isocyanate which has low volatility such as diphenylmethane diisocyanate (MDI) rather than a more volatile material such as toluene diisocyanate (TDI). Suitable isocyanates include 2,4-toluene diisocyante, 2,6-toluene diisocyanate, mixtures of these isomers, 4,4'-diphenylmethane diisocyanate, 2,4'-diphenylmethane diisocyanate, mixtures of these isomers together with possible small quantities of 2,2'-diphenylmethane diisocyanate (typical of commercially available diphenylmethane diisocyanate), and aromatic polyisocyanates and their mixtures such as are derived from phosgenation of the condensation product of aniline and formaldehyde. Typical polyols for use in the prepolymer system include polypropylene ether glycols (available from Union Carbide and from BASF Wyandotte under the tradename Pluracol ®), polytetramethylene ether glycols (Polymeg ® from the Quaker Oats Co.), polycaprolactone diols (Niax ® PCP series of polyols from Union Carbide), and polyester polyols (hydroxyl terminated polyesters obtained from esterification of dicarboxylic acids and diols such as the Rucoflex ® polyols available from Ruco division, Hooker Chemicals Co.).

An especially preferred resin for use in the casting material of the invention uses an isocyanate known as Isonate ® 143L available from the Upjohn Company (a mixture containing about 73% of MDI) and a polypropylene oxide polyol from BASF Wyandotte known as Pluracol ® P-710. To prolong the shelflife of the material, it is preferred to include from 0.1 to 1.0 percent by weight of benzoyl chloride or other suitable stabilizer.

The reactivity of the resin once it is exposed to the water curing agent can be controlled by proper catalyst. The reactivity must not be so great that: (1) a hard film quickly forms on the resin surface preventing further penetration of the water into the bulk of the resin; or (2) the cast becomes rigid before the application and shaping is complete. Good results have been achieved using dimethylethanolamine (DMEA) as the catalyst in a concentration of about 1.8 percent by weight, or more preferably, a mixture of DMEA and amine bis-(dimethylamino ethyl) ether at a concentration of 0.25 percent and 0.3 percent by weight, respectively.

Foaming of the resin should be minimized since it reduces the porosity of the cast and its overall strength. Foaming occurs because carbon dioxide is released when water reacts with isocyanate groups. One way to minimize foaming is to reduce the concentration of isocyanate groups in the prepolymer. However, to have reactivity, workability, optimum stickiness, and ultimate strength, an adequate concentration of isocyanate groups is necessary.

Although foaming is less at low resin contents, adequate resin content is required for desirable cast characteristics such as strength and resistance to unpeeling.

It has been found that most satisfactory method of minimizing foaming is to add a foam suppressor such as silicone Antifoam A (Dow Corning), DB-100 silicone fluid (Dow Corning), silicone surfactants L550 or L5303 (Union Carbide), or organic surfactants such as LK-221 ® (Air Products) to the resin. It is especially preferred to use a silicone liquid such as Dow Corning DB-100 at a concentration of about 0.1 to 1.0 percent by weight.

As normally packaged, the resin coated tape is in a roll wound up on a plastic core. For use, a roll is fully immersed in tap water for about 30 seconds. This is sufficient time for water to seep into the porous material and displace air. As long as the resin content is not too high to cause the openings in the fabric to be filled with resin, more than enough water is absorbed by the roll in this manner. When the roll is unwound during wrapping of the cast, the excess moisture coats freshly exposed resin surfaces insuring thorough wetting and rapid hardening of the cast.

Prior to applying the orthopedic cast, an inner protective sleeve is positioned about the limb or body member of the patient. The sleeve takes the form of a tubular stockinet or some other convenient form such as for example an elongated strip or bandage which may be wrapped about the body member.

The inner protective sleeve preferably comprises an air permeable fabric whereby ventilating air may pass through both the sleeve and cast to the surface of the skin. Also, the sleeve preferably comprises a fabric which does not appreciably absorb water. This structure also permits the escape of perspiration which would otherwise tend to build up and produce skin irritation and an unpleasant odor. Typically, the stockinet is a knitted or woven crystalline polypropylene material which is inherently nonwetting and permeable.

With the sleeve in a proper position, the moistened orthopedic cast material is wrapped about the body member and over the protective sleeve in a manner similar to the application of an elastic-type bandage. The cast is shaped in a manner similar to the shaping of a plaster-of-paris cast.

Eight or fewer layers of the cast material should be sufficient to form a cast having weight-bearing strength within 30 minutes, i.e., a cylindrical laminate having eight or fewer layers should support 20 pounds of pressure per inch of cylinder length. This test to determine weight-bearing strength is discussed more fully below in Example 1.

The invention may be further illustrated by the following non-limiting examples. The resin component used in these examples is based on a moisture-curing polyurethane prepolymer, but other moisture-curing systems could be used.

Three different moisture hardening polyurethane prepolymers are used in the examples and were formulated as follows:

Resin A

A moisture-curing polyurethane prepolymer was prepared from Desmodur ® E-21 commercially available from Mobay Chemical Corp. Desmodur ® E-21 is an aromatic polyisocyanate prepolymer (a mixture of p,p'-diphenylmethane diisocyanate and higher homologs) having an average equivalent weight per isocyanate group of 262 and an isocyanate content (% NCO by weight) of about 16%. It is a brown, viscous liquid. To 1000 g of Desmodur ® E-21 stirred and protected from moisture was added dropwise 10.0 ml of N,N-dimethylethanolamine to give a homogeneous mixture. No polyol was employed in this formulation.

Resin B

A polyurethane prepolymer was prepared by reaction of p,p'-diphenylmethane diisocyanate with a poly-(oxypropylene) diol to produce a viscous liquid suitable for impregnating the fabrics. A commercial form of p,p'-diphenylmethane diisocyanate was used known as Isonate ® 143L available from the Upjohn Company. Isonate ® 143L is an equilibrium mixture at room temperature containing about 73% of p,p'-diphenylmethane diisocyanate.

To 300 g of Isonate ® 143L protected from moisture under a dry nitrogen atmosphere was added slowly while stirring a solution of 5.0 ml of N,N-dimethylethanolamine in 200 g of Pluracol ® P-710, a polypropylene glycol available from BASF Wyandotte Corp., having an approximate average molecular weight of 775 and a hydroxyl number of 145. The rate of addition was adjusted to maintain the temperature of the mixture below 50° C. The resulting polyurethane prepolymer had approximately 12.5% NCO.

Resin C

Resin C is identical to Resin B except that a mixture of two tertiary amines was used as a catalyst consisting of 1.25 ml of N,N-dimethylethanolamine and 1.5 ml of 2,2'-oxybis-(N,N-dimethylethylamine). An antifoaming agent (DB-100, Dow Corning) and a stabilizer benzoyl chloride each at 0.2 percent by weight were also included.

The characteristics of the uncoated fabrics used in the examples are summarized in Table I.

TABLE I

Characteristics of Fabrics

| Fabric | Fiber | Knitting Gauge[a] | Fabric Density[b] g/in² | Approximate Wale Thickness[b] inches | Approximate Openings Dimensions[b] inches | Mesh Number Openings/in² |
|---|---|---|---|---|---|---|
| A | E-fiberglass c | 12 gg | 0.22 | 0.026–0.030 | ⅛ × 1/32 | 90 |
| B | E-fiberglass c | 12 gg | 0.23 | 0.028–0.032 | ⅛ × 1/32 | 80 |
| C | E-fiberglass c | 9 gg | 0.23 | 0.049–0.053 | ⅛ × ⅛ | 35 |
| D | E-fiberglass c | 24 gg | 0.161 | 0.022–0.024 | 1/32 × 1/32 | 140 |
| E | E-fiberglass c | 18 gg | 0.164 | 0.026–0.030 | 1/16 × 1/32 | 130 |
| F | cotton/polyester | 14 gg | 0.049 | 0.018–0.020 | ⅛ × 1/32 | 100 |
| G | Kevlar ® 49 | 18 gg | 0.115 | 0.028–0.032 | 1/16 × 1/32 | 130 |
| H | Kevlar ® 49 | 9 gg | 0.14 | 0.041–0.045 | ⅛ × 3/16 | 20 |
| I | Dacron ® | 9 gg | 0.14 | 0.046–0.050 | ⅛ × 3/16 | 20 |
| J | Nylon/polyester | 40 gg | 0.029 | 0.012 | 1/25 × 1/25 | 340 |
| K | E-Fiberglass | 48 gg | 0.139 | 0.017–0.018 | 1/50 × 1/100[d] | 380 |
| L | E-Fiberglass | 9 gg | 0.42 | 0.068–0.072 | ⅛ × 3/16 | 20 |

[a]The knitting gauge corresponds to the number of needles in a 2 inch width of the knitting machine needle bed. All fabrics are Raschel (warp) knitted.
[b]Determined by measurement of fabric in a relaxed condition, i.e., lying flat on a table and unstretched. Wale thickness is a measure of the maximum fabric thickness and not the average fabric thickness since it is the thickness of ridges in the fabric. Fabric density is the weight of a 1 inch × 1 inch swatch of the fabric.
[c]From ECC-150 or ECC-75 continuous filament fiberglass yarn.

Fabrics were oven-dried before impregnating with resin and were coated with resin promptly after removal from the oven. Fiberglass fabrics were dried overnight at 160° to 180° C. Synthetic fabrics were dried overnight at 120° C. Resin mixtures to be coated on these fabrics were formulated in a dry box with a relative humidity less than 5% at ambient temperature.

Coatings were carried out in a dry atmosphere with a relative humidity less than 20%. Resin was applied to the fabrics using either a two-roll squeeze coater or a nip-fed kiss-roll coater. The amount of resin applied was controlled by the choice of the temperature of the resin when coated, by the setting of the gap between the two coating rollers of the squeeze coater or the gap between the Doctor blade and the single roller of the nip-fed kiss-roll coater, and by adjusting the speed of the moving web. After coating, the resin content of the resin impregnated fiberglass fabrics was determined by the weight lost when a sample was burned in air in a muffle furnace held at 700° C. For the combustible synthetic fabrics, resin content was determined by extraction of the resin from a weighed sample of coated fabric using a solvent such as toluene and then weighing the dried (to a constant weight) fabric.

EXAMPLE 1

This example is included for purposes of comparison. The fabric used is illustrative of the prior art and does not meet the criteria established for the present invention.

A three-inch wide strip of the polyester/cotton Fabric F was coated with a prepolymer corresponding to Resin A to give an adhesive tape containing 53 to 54% by weight of the resin. Four-yard lengths of tape were wound on plastic cores of ½ inch diameter into rolls. Each roll was sealed in a moisture-impermeable pouch for storage. The hardening and strength properties of the tape were determined by forming cyclinder casts from the moistened tape and then measuring the load bearing ability 15 minutes and 24 hours later. According to the procedure, a roll of tape was removed from its pouch, immersed in room temperature tap water for 30 seconds and then wrapped into a 3-inch long (the width of the tape) cylinder on a 2-inch diameter mandrel. After 15 minutes or 24 hours (measured from the beginning of the 30 second immersion period), compressive loads were applied to the cylinder cast along its exterior and parallel to its axis. The cylinder was supported in a fixture with two "knife" (⅛ inch radius) edges spaced 1.6 inches apart parallel to the cylinder axis. A third "knife" edge was centered over the top of the cylinder also parallel to the axis. Force was applied to the cylinder along the knife edges. The maximum load capable of being sustained was measured using a Dillon dynamometer. The results for casts of various layers are reported in the following Table II.

TABLE II

Rigidity of Cylinder Casts from Synthetic Fabric of Example 1

| Number of layers in cast | Compressive Load Bearing Ability pounds per inch of cast length | | Weight of 3" long, 2" diam. cylinder cast, g |
|---|---|---|---|
| | 15 min. after immersion[a] | 24 hr. after immersion[b] | |
| 5 | 1.9 | 3.3 | 10.6 |
| 8 | 6.0 | 9.3 | 17.0 |
| 12 | 15.5 | 22.9 | 25.8 |
| 16 | — | 41.3 | 35.8 |

[a]Average of 8 determinations
[b]Average of 4 determinations except for 16 layer ring which was a single sample.

It is evident that in every case the 15-minute value is more than 50% of the 24-hour value indicating that a substantial fraction of the water-induced polymerization has occurred by 15 minutes. However, until 12 or more layers of the tape have been applied, the rigidity is not sufficient for most orthopedic casting applications, i.e., about 20 lbs/inch or more of load bearing ability as measured by this test. The following example shows that sufficient load bearing can be obtained with fewer layers using a fabric according to the present invention.

EXAMPLE 2

Under dry conditions, freshly oven-dried fiberglass (Fabric A, 3 inches wide) was impregnated (using a two roller coater head) with Resin A to obtain a resin content of 45.8% as a percent by weight of the coated tape. Four-yard long rolls were prepared and packaged as described in Example 1. Following a 30-second immersion of a roll in tap water, 5-layer cylinder casts of 2-inch inside diameter were made and tested at various time intervals for load bearing ability (as described in Example 1). These results are summarized in the following Table III.

TABLE III

Rigidity of Cylinder Casts * from Tape of Example 2

| Time After Immersion | Compressive Load pounds/inch of cylinder length |
|---|---|
| 15 min. | 8.7 |
| 30 min. | 15.7 |
| 60 min. | 23.0 |
| 24 hr. | 50.2 |

*Five-layer cylinder casts 3 inches long and 2 inches in diameter were made immediately after immersion of a roll of tape in 80° F. water for 30 seconds. Each value is for one cast except the 24-hour value which is the average of 6 samples. The average weight of these casts when dry was 40.2 g.

The foregoing data indicate:
1. The 15-minute rigidity greatly exceeds that for a 5-layer cylinder cast of Example 1.
2. The load bearing ability exceeds 20 lbs/inch after about 1 hour.
3. The 15-minute load is only 17% of the overnight value, which indicates that at 15 minutes significant hardening has still to take place.

EXAMPLE 3

A 3-inch wide strip of freshly dried Fabric B was impregnated with Resin A yielding a tape containing 46.1% by weight of resin. Cylinder casts were made immediately from a 4-yard roll of tape following a 30 second immersion in 80° F. water. The load bearing ability was measured as in Example 1 at various time intervals following immersion. The results are summarized in the following Table IV.

TABLE IV

Rigidity of Cylinder Casts * from Tape of Example 3

| Time After Immersion | Compressive Load pounds/inch of cylinder length |
|---|---|
| 15 min. | 8.3 |
| 30 min. | 13.3 |
| 60 min. | 21.0 |
| 24 hr. | 58.4 |

*Five-layer cylinder casts 3 inches long and 2 inches in diameter. The average weight of dry casts was 44.8 g.

Comparison with Table III shows that although the 24 hour rigidity has increased due to the increased weight of the fabric, the 15-minute rigidity is slightly reduced below that for the thinner Fabric A. The increased fiberglass thickness and the slightly decreased mesh number that introduces more material in each layer of a cast decreases the rate of hardening.

EXAMPLE 4

This example shows the effect of variations in fabric parameters, i.e., mesh size and thickness upon the rate of hardening and rigidity of the finished cast.

Dried fiberglass Fabrics A through E of Table I were individually coated with Resin B. Resin contents were held as closely similar as possible, although fabric C, due to its low surface area, was not easy to impregnate. Cylinder casts were made immediately after a 30-second immersion in water at 80° F.

Because of the different thicknesses of fabrics, different numbers of layers were used to obtain cylinder casts of comparable weight. Thus, five layers for Fabrics A and B corresponded to 4 layers for Fabric C (the thickest fabric) and 6 layers for Fabrics D and E. Load bearing was determined as in Example 1, 15 minutes, 30 minutes and 24 hours following immersion. The results are summarized in the following Table V.

TABLE V

Rigidities of Cylinder Casts of Example 4

| Fabric | Resin Content % by weight | Layers | Cast Weight, g/inch of length | Compressive Load Bearing Ability, pounds/inch of cylinder length | | |
|---|---|---|---|---|---|---|
| | | | | 15 minutes | 30 minutes | 24 hours |
| A | 44.8 | 5 | 13.4 | 6.5 | 10.0 | 47.0 |
| B | 45.1 | 5 | 14.9 | 7.5 | 12.0 | 54.7 |
| C | 35.9 | 4 | 12.8 | 3.0 | 12.0 | 63.0 |
| D | 47.4 | 6 | 11.6 | 19.0 | 27.8 | 70.0 |
| E | 48.2 | 6 | 12.6 | 14.0 | 21.3 | 69.6 |

These fabrics fall into three classes with respect to their surface area to volume ratios. Fabric C has the lowest surface area per unit volume (approximately 320 $in^2/in^3$). Fabrics A and B have an intermediate value (about 390 $in^2/in^3$) and Fabrics D and E have the highest surface to volume ratio (about 540 $in^2/in^3$). The rate at which rigidity is developed shortly after exposure to water differs for these classes of fabrics. This can be seen by comparing the ratio of the 15-minute rigidity to the 24-hour rigidity (divided by cast weight) as shown in the following Table VI (using the data of Table V). Another correlation to early development of rigidity for this example is the mesh number divided by the approximate wale thickness (shown in Table VI, also).

TABLE VI

| Fabric | Early Rigidity (15 min. Rigidity) (24 hr. Rigidity) Cast Weight | Mesh Number | Approximate Wale Thickness | Mesh Number Wale Thickness |
|---|---|---|---|---|
| A | 0.0103 | 90 | 0.028 | 3200 |
| B | 0.0092 | 80 | 0.030 | 2700 |
| | 0.0151* | | | |
| C | 0.0037 | 35 | 0.051 | 690 |
| D | 0.0234 | 140 | 0.023 | 6100 |
| E | 0.0160 | 130 | 0.028 | 4600 |
| | 0.0211* | | | |
| | 0.0226* | | | |

*Results from Example 5 below.

It is evident also from Table V that with Fabrics D and E, more than 20 lbs/inch of rigidity are developed in a 6-layer cast within 30 minutes, which exceeds the previously stated criterion for orthopedic cast function. With Fabrics A–D, a greater number of layers is required for finished casts meeting this criterion.

EXAMPLE 5

The factors affecting fabric choice apply when the prepolymer is more reactive. This is shown by using Resin C which contains two amine catalysts. The combination of catalysts causes polymerization to be faster than for Resin B.

Fabrics B and E were impregnated with Resin C, and cylinder casts were made (5 layers for Fabric B and 6 layers for Fabric E). The rigidities attained within 15 minutes are improved over Resin B (Table V), but the coarser, thicker Fabric B still lags behind Fabric E when corrections for cast weight are made. The results are summarized in the following Table VII.

TABLE VII

Rigidities of Cylinder Casts of Example 5

| Fabric | Resin Content % by weight | Layers | Cast Weight g/inch of length | Compressive Load Bearing Ability, pounds/inch of cylinder length | | |
|---|---|---|---|---|---|---|
| | | | | 15 minutes | 30 minutes | 24 hours |
| B | 45.3% | 5 | 14.7 | 11.7 | 19.8 | 52.7 |
| E | 44.6% | 6 | 12.0 | 14.0 | 24.7 | 55.3 |
| E | 46.2% | 6 | 12.5 | 18.7 | 36.7 | 66.1 |

EXAMPLE 6

This example shows that in the case of another high modulus fiber, namely Kevlar® 49, the fabric properties are again important in determining the rate of cast rigidification. This example also compares the relative performance in a cast of fibers of high modulus and of low modulus.

Fiberglass Fabric C and synthetic fabrics G, H, I and J, were dried and impregnated with Resin C as previously described. The specific gravity and initial modulus of elasticity for the varius fibers are given in the following Table IX.

TABLE IX

| Fiber | Fiber Properties | |
|---|---|---|
| | Specific Gravity | Initial Modulus of Elasticity lbs/in$^2$ × 10$^6$ |
| Kevlar ® 49 | 1.44 | 18 |
| E-Fiberglass | 2.54 | 10 |
| Kuralon PVA | 1.26 | 3.0 |
| Dacron ® | 1.38 | 2.0 |
| Cotton | 1.71 | 1.0 |
| Nylon | 1.14 | 0.6 |

Since the specific gravities of the various fibers differ, resin contents were adjusted so that they were comparable on a volume basis, i.e., the ratio of the volume of resin to the volume of fabric is comparable from fabric to fabric, and the resin available to form interlaminate bonds is approximately equivalent in amount.

Fabrics G (Kevlar ® 49) and E (fiberglass) are of comparable knit structure. Therefore, casts of six layers were made from resin-impregnated Fabric G for comparison with those of Example 5 of Fabric E. Fabrics H (Kevlar ® 49), C (fiberglass), and I (Dacron ®) were similarly of comparable knit patterns so that cylinder casts of 5 layers were made from each. Fabric J (nylon/polyester) is a lighter weight fabric than the others and has a finer mesh. Consequently, cylinders of 10 and 20 layers were fabricated from it. The rigidities of these casts are reported in the following Table X.

TABLE X

| | Rigidities of Cylinder Casts of Example 6 | | | | | |
|---|---|---|---|---|---|---|
| | Resin Content | | Cast Weight g/inch of | Compressive Load Bearing Ability, pounds/inch of cylinder length. | | |
| Fabric | % by weight | Layers | length | 15 minutes | 30 minutes | 24 hours |
| G (Kevlar ® 49) | 55.3% | 6 | 11.5 | 25.3 | 38.4 | 92.8 |
| H (Kevlar ® 49) | 51.3% | 5 | 11.3 | 15.6 | 31.1 | 96.4 |
| E (glass) | 44.6% | 6 | 12.0 | 14.0 | 24.7 | 55.3 |
| C (glass) | 40.7% | 5 | 19.6 | 12.8 | 22.4 | 160.0 |
| I (Dacron ®) | 52.4% | 5 | 11.2 | 10.1 | 16.9 | 52.1 |
| J (nylon/polyester) | 64.7% | 10 | 6.6 | 5.5 | 7.6 | 18.9 |
| | | 20 | 14.0 | 27.3 | — | 81.8 |

The casts of the two Kevlar ® 49 fabrics are of comparable weight, so a comparison of absolute rigidities is meaningful. Table X shows that while the overnight rigidities of the two materials are similar, the rigidity attained 15 minutes following wetting with water is substantially higher for Fabric G, the thinner, finer mesh fabric. Table IX indicates that Kevlar ® 49 has a somewhat higher modulus of elasticity than fiberglass so that it would be expected that Kevlar-containing casts would have higher rigidities than for similar structured fabrics constituted of fiberglass. This is, indeed, the case as shown by a comparison of rigidities in Table X; casts of Fabric G support higher loads than for Fabric E. Fabric H supports more than will its glass counterpart, Fabric C, of equivalent cast weight.

The lower modulus fibers do not produce acceptably rigid casts. Thus, Fabric I of Dacron ® does not compare favorably with similar structure Kevlar ® 49 or fiberglass fabrics when used in a cast. The thin, fine mesh Fabric J, although achieving about 30% of its ultimate rigidity in the first 15 minutes following wetting with water, does not produce a rigid cast with even 10 layers of material. A cast with rigidity comparable to that produced by Fabric G would not only require numerous (about 20) layers of Fabric J, but the cast would be heavier than the Kevlar ® 49 or fiberglass cast despite the lower specific gravity of the nylon/polyester fiber combination.

Another disadvantage of Fabric J was that it gave casts that were occluded and not porous. This is due to the high mesh number of this fabric coupled with the large number of overlapping layers needed in the cast. Furthermore, water did not completely penetrate the roll of impregnated tape when it was dipped in water; it was necessary to wet each layer individually with water as this tape was wrapped into a cast rendering cast application inefficient.

EXAMPLE 7

This example examines a wider range of fiberglass fabrics. The extremes of the range are represented by Fabric K (finest) and Fabric L (coarsest) whose characteristics are listed in Table I. Dried Fabrics K, E, C and L were impregnated as described in previous examples with Resin A (Desmodur ® E-21 containing 1 ml of N,N-dimethylethanolamine per 100 g of resin). Fabrics A and B had been coated previously with resin A (Examples 2 and 3). Cylinder casts were made promptly following wetting of the tape with water. The load bearing abilities were measured as described previously. Results obtained are summarized in the following Table XII in order of increasing fabric coarseness, i.e., increasing thickness and openness. Data from Examples 2 and 3 are included for comparison.

TABLE XII

| | Rigidities of Cylinder Casts of Example 7 | | | | | | |
|---|---|---|---|---|---|---|---|
| | Resin Content | | Cast Weight g/inch of | Compressive Load Bearing Ability pounds/inch of cylinder length | | | (15 min. Rigidity) (24 hr. Rigidity) |
| Fabric | % by weight | Layers | length | 15 minutes | 30 minutes | 24 hrs. | Cast Weight |
| K | 39.6% | 7 | 11.0 | 37.9 | 43.7 | 61.9 | 0.0557 |
| | 45.1% | 7 | 11.6 | 40.3 | 48.6 | 93.2 | 0.0373 |
| E | 37.9% | 6 | 12.6 | 17.5 | 26.6 | 48.4 | 0.0287 |
| A | 45.8% | 5 | 13.4 | 8.7 | 15.7 | 50.2 | 0.0129 |
| B | 46.1% | 5 | 14.9 | 8.3 | 13.3 | 58.4 | 0.0095 |
| C | 45.4% | 4 | 16.7 | 12.8 | 18.7 | 101.4 | 0.0076 |
| L | 39.3% | 3 | 17.6 | 10.3 | 20.8 | 87.1 | 0.0067 |

The finer mesh, thinner fabrics listed first in the table attain rigidity faster for a given weight of cast material than the coarser ones, with Fabric K being fastest. However, Fabric K produces a cast that is not porous whereas all other fabrics of Table XII gave excellent air permeability and porosity. With mesh numbers greater than about 200, casts will not be porous.

EXAMPLE 8

This example illustrates the factors affecting the porosity of casting tapes made with Fabric K. Dry fabric K was coated with Resin C as described previously with various coating speeds and gap settings to obtain tapes with differing resin contents. The following Table XIII gives resuts for water taken into the roll upon immersion, cast rigidities, and other properties relating to porosity and strength. When the resin content was reduced enough to achieve some cast porosity, the test casts were very weak even after 24 hours and delaminated. When the resin content was raised in order to make sufficiently strong casts, all porosity was lost.

TABLE XIII

Properties of Cylinder Casts Using Fabric K

| Resin Content % by weight | Cast Weight g/inch of length (7 layers) | Compressive Load Bearing Ability, pounds/inch of cylinder length | | Water Up-Take Upon Immersion % by weight | Cast Porosity |
|---|---|---|---|---|---|
| | | 15 minutes | 24 hours | | |
| 29.6% | 9.2 | 3.5 | 18.7 | 46.6% | slightly porous and delaminates |
| 39.7% | 10.2 | 22.7 | 46.1 | 21.8% | non porous |
| 46.9% | 12.1 | 37.9 | 96.0 | 19.8% | non porous |
| 53.3% | 13.4 | 44.8 | 105.0 | 5.8% | non porous |

What is claimed is:

1. An orthopedic casting material comprising a fabric made from a fiber having an initial modulus of elasticity greater than $8 \times 10^6$ pounds per square inch, said fabric having a thickness between 0.020 and 0.045 inch and a mesh size of 20 to 200 openings per square inch and a reactive fluid polyisocyanate prepolymer resin impregnated in said fabric which hardens when said resin is wetted with water.

2. The orthopedic casting material according to claim 1 wherein said polyisocyanate prepolymer comprises polypropylene oxide polyol endcapped with diphenylmethane diisocyanate.

3. The orthopedic casting material according to claim 1 wherein said resin further comprises an anti-foaming agent.

4. The orthopedic casting material according to claim 3 wherein said anti-foaming agent is a silicone.

5. The orthopedic casting material according to claim 1 wherein said resin further comprises a catalyst to control hardening time.

6. The orthopedic casting material according to claim 5 wherein said catalyst is dimethylethanolamine.

7. The orthopedic casting material according to claim 6 wherein said catalyst is a mixture of dimethylethanolamine and amino bis-(dimethylaminoethyl) ether.

8. A method of forming an orthopedic cast on a body member comprising the steps of:
 1. covering said body member with an inner protective sleeve comprising an air permeable fabric; and
 2. wrapping said body member with an orthopedic casting material comprising a fabric made from a fiber having an initial modulus of elasticity greater than $8 \times 10^6$ pounds per square inch, said fabric having a thickness between 0.020 and 0.045 inch and a mesh size of 20 to 200 openings per square inch and a reactive fluid polyisocyanate prepolymer resin impregnated in said fabric which has been wetted with water to harden said resin after said wrapping is completed.

* * * * *